(12) United States Patent
Garrett et al.

(10) Patent No.: US 10,383,921 B2
(45) Date of Patent: Aug. 20, 2019

(54) LEVERAGING OXIDATIVE STRESS PATHWAYS IN LACTIC ACID BACTERIA TO PROMOTE GUT HOMEOSTASIS

(71) Applicants: President and Fellows of Harvard College, Cambridge, MA (US); Compagnie Gervais Danone, Paris (FR)

(72) Inventors: Wendy S. Garrett, Brookline, MA (US); Patrick Veiga, Boston, MA (US); Sonia Arora Ballal, Brookline, MA (US); Johan van Hylckama Vlieg, Chavenay (FR); Gaëlle Quéré, Saclay (FR); Peggy Garault, Montlhéry (FR)

(73) Assignees: PRESIDENT AND FELLOWS OF HARVARD COLLEGE, Cambridge, MA (US); COMPAGNIE GERVAIS DANONE, Paris (FR)

( * ) Notice: Subject to any disclaimer, the term of this patent is extended or adjusted under 35 U.S.C. 154(b) by 0 days.

(21) Appl. No.: 14/912,033

(22) PCT Filed: Aug. 13, 2014

(86) PCT No.: PCT/US2014/050946
§ 371 (c)(1),
(2) Date: Feb. 12, 2016

(87) PCT Pub. No.: WO2015/023788
PCT Pub. Date: Feb. 19, 2015

(65) Prior Publication Data
US 2016/0193303 A1     Jul. 7, 2016

Related U.S. Application Data

(63) Continuation-in-part of application No. PCT/US2013/054811, filed on Aug. 13, 2013.

(51) Int. Cl.
    *A61K 38/44*     (2006.01)
    *C12N 9/02*     (2006.01)
    *C12Q 1/02*     (2006.01)

(52) U.S. Cl.
    CPC .......... *A61K 38/446* (2013.01); *C12N 9/0089* (2013.01); *C12Q 1/025* (2013.01);
    (Continued)

(58) Field of Classification Search
None
See application file for complete search history.

(56) References Cited

U.S. PATENT DOCUMENTS 5,540,911 A * 7/1996 Hartman .............. C12N 9/0089
    424/94.4
6,303,572 B1    10/2001 Rowe
(Continued)

FOREIGN PATENT DOCUMENTS

EP      0289667      11/1988
FR      2807 446 A1      10/2001
(Continued)

OTHER PUBLICATIONS

Uniprot Accession No. G6FDQ4_LACLL, published Jan. 25, 2012.*
(Continued)

*Primary Examiner* — Richard C Ekstrom
(74) *Attorney, Agent, or Firm* — Nixon Peabody LLP

(57) ABSTRACT

Disclosed herein are compositions and methods for providing an antioxidant effect to a subject, e.g., modulating or otherwise improving oxidative stress pathways and/or neutralizing or reducing damaging reactive oxygen species (ROS).

7 Claims, 11 Drawing Sheets

Specification includes a Sequence Listing.

(52) U.S. Cl.
CPC .... *C12Y 115/01001* (2013.01); *G01N 2333/315* (2013.01); *G01N 2333/335* (2013.01); *G01N 2333/90283* (2013.01)

(56) References Cited

U.S. PATENT DOCUMENTS

| | | | |
|---|---|---|---|
| 6,534,054 | B2 | 3/2003 | Olshenitsky et al. |
| 6,544,509 | B2 | 4/2003 | Olshenitsky et al. |
| 6,746,671 | B2 | 6/2004 | Steidler et al. |
| 7,504,251 | B2 | 3/2009 | Olshenitsky et al. |
| 2002/0019043 | A1* | 2/2002 | Steidler .............. A61K 38/2066 435/252.3 |
| 2008/0181872 | A1 | 7/2008 | Doroudchi |
| 2009/0324776 | A1 | 12/2009 | Marchal et al. |
| 2010/0080774 | A1 | 4/2010 | Steidler et al. |
| 2010/0260706 | A1 | 10/2010 | Bogin et al. |

FOREIGN PATENT DOCUMENTS

| | | |
|---|---|---|
| WO | WO 1997/16529 | 5/1997 |
| WO | 2001/077334 A2 | 10/2001 |
| WO | WO 2012/080789 | 6/2012 |
| WO | WO 2015/023268 | 2/2015 |
| WO | WO 2015/023788 | 2/2015 |

OTHER PUBLICATIONS

Ballal, et al., "Host lysozyme-Mediated Lysis of Lactococcus Colitis-Attenuating Superoxide Dismutase to Inflamed Colons," *Proceedings of the National Academy of Sciences*, 112(25):7803-7808, (2015).

Guo, et al., "Herpes Simplex Virus Containing the Human Manganese Superoxide Dismutase Transgene (HSV-MnSOD) Protects the Intestine from Irradiation Damage," *Molecular Therapy*, 5(55):p. S272, (2002).

Leblanc, et al., "Use of Superoxide Dismutase and Catalase Producing Lactic Acid Bacteria in TNBS Induced Crohn's Disease in Mice," *J. Biotech.*, 151(3):286-293, (2010).

Seixas-Silva, et al., "Manganese Superoxide Dismutase-Plasmid/Lipsome (MnSOD-PL) Complex Prevents Irradiation-Induced Mucositis of the Oral Cavity," *Molecular Therapy*, 5(S5):p. S272, (2002).

Watterlot, et al., "Intragastric Administration of a Superoxide Dismutase-Producing Recombinant Lactobacillus Casel BL23 Strain Attenuates DSS Colitis in Mice," *Intl. J. of Food Micro.*, 144(1):35-41, (2010).

Supplementary European Search Report from EP 14836807.9, dated Jan. 10, 2017.

Akyol, et al., "The effect of exogenous superoxide generator chemicals on sodA and flpA promoters expression in *Lactococcus lactis*," Journal of Cell and Molecular Biology, 5: 87-93, (2006).

Bruno-Barcena, et al, "Expression of a Heterologous Manganese Superoxide Dismutase Gene in Intestinal Lactobacilli Provides Protection Against Hydrogen Peroxide Toxicity," Applied and Environmental Microbiology, 70(8): 4702-4710, (2004).

del Carmen, et al., "Evaluation of the anti-inflammatory effect of milk fermented by a strain of IL-10-producing Lactococcus lactis using a murine model of Crohn's disease," J. Mol. Microbiol. Biotechnol., 21(3-4): 138-46. Doi: 10.1159/000333830. Epub Jan. 31, 2012., Abstract.

Garrett, et al., "Colitis-Associated Colorectal Cancer Driven by T-bet Deficiency in Dendritic Cells," Cancer Cell 16: 208-219 (2009).

Garrett, et al., "Communicable Ulcerative Colitis Induced by T-bet Deficiency in the Innate Immune System," Cell 131: 33-45 (2007).

Garrett, et al., "T-bet-/-RAG2-/-Ulcerative Colitis: the role of T-bet as a peacekeeper of host-commensal relationships," Cyokine 48(1-2): 144-147 (2009).

Han, et al. "Improvement of an Experimental Colitis in Rats by Lactic Acid Bacteria Producing Superoxide Dismutase," Inflamm Bowel Dis. 12(11): 1044-1052 (2006).

Roy, et al., "Cloning and Expression of the Manganese Superoxide Dismutase Gene of *Escherichia coli* in Lactococcus Lactis and Lactobacillus Gasseri," Molecular and General Genetics 239: 33-40 (1993).

Sanders et al. "Stress Response in Lactococcus lactis: Cloning, Expression Analysis, and Mutation of the Lactococcal Superoxide Dis mutase Gene," Journal of Bacteriology 177(18): 5254-5260 (1995).

Smith, et al., "Molecular Mechanisms of Stress Resistance in *Lactococcus lactis*," Current Research, Technology and Education Topics in Applied Microbiology and Microbial Biotechnology, A. Mendez-Vilas (Ed.), pp. 1106-1118, (Jan. 2010).

International Search Report for International Application PCT/US2013/054811, dated Aug. 12, 2014.

International Search Report for International Application PCT/US2014/050946, dated Dec. 31, 2014.

International Preliminary Report on Patentability PCT/US2013/054811, dated Feb. 25, 2016.

International Preliminary Report on Patentability PCT/US2014/050946, dated Feb. 25, 2016.

Qin, et al., "A Metagenome-Wide Association Study of Gut Microbiota in Type 2 Diabetes," *Nature*, 000:1-6, (2012).

Tjong, et al., "Role of Neuronal Nitric Oxide Synthase in Colonic Distension-Induced Hyperalgesia in Distal Colon of Neonatal Maternal Separated Male Rats," *Neurogastroenterol Motil.*, 23(7):666-e278, (Jul. 2011).

Uskova M.A. Izuchenie svoistv probiotichskikh molochnokislykh bacteriy kak biologichsky aktivnykh komponentov pishchi. "Studying the properties of probiotic lactic acid bacteria as biologically active components of food" Extended abstract of PhD dissertation, Moscow, 2010, pp. 1, 10-26. English Translation Included.

Ballal et al., "Host lysozyme-mediated lysis of Lactococcus lactis facilitates delivery of colitis-attenuating superoxide dismutase to inflamed colons." PNAS 112(25):7803-7808 (2015).

Bolotin et al. "The complete genome sequence of the lactic acid bacterium *Lactococcus lactis* ssp. lactis IL1403." Genome Research 11(5):731-753 (2001).

Guo et al., "831: Herpes Simplex Virus Containing the Human Manganese Superoxide Dismutase Transgene (HSV-MnSOD) Protects the Intestine from Irradiation Damage." Molecular Therapy 5(S5):S272 (2002).

Leblanc et al., "Use of superoxide dismutase and catalase producing lactic acid bacteria in TNBS induced Crohn's disease in mice." Journal of Biotechnology 151(3):287-293 (2011).

McNulty et al., "The impact of a consortium of fermented milk strains on the gut microbiome of gnotobiotic mice and monozygotic twins." Science Translational Medicine 3(106):106ra106 (2011).

Seixas-Silva et al., "830: Manganese Superoxide Dismutase-Plasmid/Liposome (MnSOD-PL) Complex Prevents Irradiation-Induced Mucositis of the Oral Cavity." Molecular Therapy 5(S5):S272 (2002).

Veiga et al. "*Bifidobacterium animalis* subsp. lactis fermented milk product reduces inflammation by altering a niche for colitogenic microbes." PNAS 107(42):18132-18137 (2010).

Veiga et al. "*Bifidobacterium animalis* subsp. lactis fermented milk product reduces inflammation by altering a niche for colitogenic microbes." PNAS 107(42):18132-18137 (2010)—Supplemental Material.

Watterlot et al., "Intragastric administration of a superoxide dismutase-producing recombinant Lactobacillus casei BL23 strain attenuates DSS colitis in mice." International Journal of Food Microbiology 144(1):35-41 (2010).

* cited by examiner

Superoxide dismutase [Lactococcus lactis subsp. cremoris CNCM I-1631].
ACCESSION    EHE92936
VERSION      EHE92936.1  GI:354693159
SEQ ID NO: 1

1 maftlpelpy apnalepffd eatmrlhhgk hhqtyvnnln aaiekhneid disleelltd
 61 lsaipedirt avrnnggghl nhsqfwlwlr pntdgsenha dgeigdaiak efgsfetfkt
121 efkaaatgrf gsgwawlvvd eagklkvvst anqdnpiseg itpvlgldvw ehayylkyhn
181 vrpdyieaff nlvnwdkvne lyakak

FIG. 9

Superoxide dismutase [Lactococcus lactis subsp. cremoris CNCM I-1631]
Contig068, whole genome shotgun sequence.
ACCESSION   AGHX01000068.1 - 58907-59527
SEQ ID NO: 2

```
58907                                                        ttat tttgctttag
58921 cataaagttc gttaactttα tcccagttta caaggttaaa gaatgcttca atgtaatcag
58981 gacgtacatt gtgatattta agatagtaag catgttccca aacatcaagt cctaaaactg
59041 gtgtcaaccc ttcagaaatt ggattatctt gatttgcagt tgatacaact ttcaattttc
59101 cagcttcatc aacaactaac caagcccatc ctgaaccaaa acgacctgtg gctgcagctt
59161 taaattctgt tttgaaagtt tcaaaactac caaattcttt cgcaattgca tccccaattt
59221 cgccgtcagc atggttttca gaaccgtcag tgttttggacg aagccaaagc cagaattgac
59281 tatggttcaa atgaccacca ccattgttac gaacagctgt acgaatgtct tctggaattg
59341 ctgacaaatc tgtcaataat tcttcaaggc taaggtcatc aagttcatta tgttttttcaa
59401 ttgctgcatt aagattattc acataagttt gatgatgttt tccatgatgc aaaacgcattg
59461 ttgcttcgtc aaagaaaggt tcaagcgcat ttggcgcgta tggaagttca ggtaatgtaa
59521 atgccat
```

*FIG. 10*

Superoxide dismutase [Lactococcus lactis subsp. cremoris CNCM I-1631]
Contig068, whole genome shotgun sequence.
ACCESSION   AGHX01000068.1 - 58907-58976
SEQ ID NO: 3

58907 ttattttgct ttagcataaa gttcgttaac tttatcccag tttacaaggt taaagaatgc ttcaatgtaa

FIG. 11

```
                       SEQUENCE LISTING

<160> NUMBER OF SEQ ID NOS: 3

<210> SEQ ID NO 1
<211> LENGTH: 206
<212> TYPE: PRT
<213> ORGANISM: Lactococcus lactis CNCM I-1631

<400> SEQUENCE: 1

Met Ala Phe Thr Leu Pro Glu Leu Pro Tyr Ala Pro Asn Ala Leu Glu
1               5                   10                  15

Pro Phe Phe Asp Glu Ala Thr Met Arg Leu His His Gly Lys His His
                20                  25                  30

Gln Thr Tyr Val Asn Asn Leu Asn Ala Ala Ile Glu Lys His Asn Glu
            35                  40                  45

Leu Asp Asp Leu Ser Leu Glu Glu Leu Leu Thr Asp Leu Ser Ala Ile
        50                  55                  60

Pro Glu Asp Ile Arg Thr Ala Val Arg Asn Asn Gly Gly Gly His Leu
65                  70                  75                  80

Asn His Ser Gln Phe Trp Leu Trp Leu Arg Pro Asn Thr Asp Gly Ser
                85                  90                  95

Glu Asn His Ala Asp Gly Glu Ile Gly Asp Ala Ile Ala Lys Glu Phe
            100                 105                 110

Gly Ser Phe Glu Thr Phe Lys Thr Glu Phe Lys Ala Ala Ala Thr Gly
        115                 120                 125

Arg Phe Gly Ser Gly Trp Ala Trp Leu Val Val Asp Glu Ala Gly Lys
    130                 135                 140

Leu Lys Val Val Ser Thr Ala Asn Gln Asp Asn Pro Ile Ser Glu Gly
145                 150                 155                 160

Leu Thr Pro Val Leu Gly Leu Asp Val Trp Glu His Ala Tyr Tyr Leu
                165                 170                 175

Lys Tyr His Asn Val Arg Pro Asp Tyr Ile Glu Ala Phe Phe Asn Leu
            180                 185                 190

Val Asn Trp Asp Lys Val Asn Glu Leu Tyr Ala Lys Ala Lys
        195                 200                 205

<210> SEQ ID NO 2
<211> LENGTH: 621
<212> TYPE: DNA
<213> ORGANISM: Lactococcus lactis CNCM I-1631

<400> SEQUENCE: 2
ttattttgct ttagcataaa gttcgttaac tttatcccag tttacaaggt taaagaatgc        60
ttcaatgtaa tcaggacgta cattgtgata tttaagatag taagcatgtt cccaaacatc       120
```

```
aagtcctaaa actggtgtca acccttcaga aattggatta tcttgatttg cagttgatac    180
aactttcaat tttccagctt catcaacaac taaccaagcc catcctgaac caaaacgacc    240
tgtggctgca gctttaaatt ctgttttgaa agtttcaaaa ctaccaaatt ctttcgcaat    300
tgcatcccca atttcgccgt cagcatggtt ttcagaaccg tcagtgtttg gacgaagcca    360
aagccagaat tgactatggt tcaaatgacc accaccattg ttacgaacag ctgtacgaat    420
gtcttctgga attgctgaca aatctgtcaa taattcttca aggctaaggt catcaagttc    480
attatgtttt tcaattgctg cattaagatt attcacataa gtttgatgat gttttccatg    540
atgcaaacgc attgttgctt cgtcaaagaa aggttcaagc gcatttggcg cgtatggaag    600
ttcaggtaat gtaaatgcca t                                              621

<210> SEQ ID NO 3
<211> LENGTH: 70
<212> TYPE: DNA
<213> ORGANISM: Lactococcus lactis CNCM I-1631

<400> SEQUENCE: 3
ttattttgct ttagcataaa gttcgttaac tttatcccag tttacaaggt taaagaatgc    60
ttcaatgtaa                                                          70
```

LEVERAGING OXIDATIVE STRESS PATHWAYS IN LACTIC ACID BACTERIA TO PROMOTE GUT HOMEOSTASIS

RELATED APPLICATIONS

This application is a national stage filing under 35 U.S.C. 371 of International Application No. PCT/US2014/050946, filed Aug. 13, 2014, which is a continuation-in-part of International Application No. PCT/US2013/054811, filed Aug. 13, 2013, the entire teachings of which are incorporated herein by reference. International Application PCT/US2014/050946 was published under PCT Article 21(2) in English.

BACKGROUND OF THE INVENTION

The Centers for Disease Control and Prevention estimates that as many as 1.4 million patients in the United States are affected by inflammatory bowel disease. The two most common forms of inflammatory bowel disease, ulcerative colitis and Crohn's disease, are each characterized by recurrent inflammation of the gastrointestinal tract.

Ulcerative colitis is characterized by a diffuse mucosal inflammation that is confined to the colon and rectum and is associated with diarrhea accompanied by mucus and blood discharge, cramping, abdominal pain, inflammation and edema of the mucous membrane and patches of ulceration. Crohn's disease primarily affects the ileum and jejunum and to a lesser extent the colon and is frequently associated with diarrhea, cramping, loss of appetite and weight loss with local abscesses and scarring.

In response to acute and chronic inflammation, a subject (e.g., a mammal) often produces reactive oxygen species (e.g., superoxide and hydrogen peroxide) capable of causing tissue injury, particularly in subjects that cannot effectively degrade or neutralize such reactive oxygen species. The accumulating reactive oxygen species promote inflammation by their ability to oxidize and degrade essential cellular constituents, including the induction of damage to cellular nucleic acids. In addition, reactive oxygen species may act as pro-inflammatory signaling agents and may also activate certain transcription factors that are known to up-regulate the expression of genes involved in the inflammatory response (Connor E M, et al. *Inflammatory Bowel Diseases;* 2(2): 133-147 (1996)). Because the gastrointestinal tract is subject to oxidative stress in response to insults or other pathological conditions, the presence and accumulation of reactive oxygen species may further contribute to the inflammation that characterizes inflammatory bowel disease.

There is a need for methods of providing an antioxidant effect, as well as a need for as methods of preventing and/or treating the effects of oxidation, for example the effects of oxidation resulting from or related to reactive oxygen species and/or oxidative stress.

Novel therapies or preventative measures are also needed for treating and/or preventing inflammatory diseases affecting the gastrointestinal tract, such as inflammatory bowel disease. Particularly needed are safe and effective therapies that are capable of mitigating (e.g., reducing or improving symptoms) the damaging effects that reactive oxygen species exert on the cells and tissues of the gastrointestinal tract. Also needed are new therapies that can successfully induce remission and prevent relapse of inflammatory bowel disease.

SUMMARY OF THE INVENTION

Provided herein are novel compositions (e.g., preventative or therapeutic compositions) and methods of treating or preventing inflammatory conditions, and in particular those inflammatory conditions affecting the cells and tissues of the gastrointestinal tract (e.g., ulcerative colitis, Crohn's disease, diversion colitis, pouchitis, irritable bowel syndrome, cancer of the gastrointestinal tract, obesity and type II diabetes). In certain embodiments, the disclosed compositions and methods can be used to provide an antioxidant effect (e.g., reduce or otherwise neutralize the damaging effects of reactive oxygen species (ROS), reduce oxidative stress, etc.) in a subject, and/or to induce remission and/or prevent relapse of inflammatory bowel diseases.

In some embodiments the present inventions relate to enzymes (e.g., superoxide dismutase (SOD) enzymes such as superoxide dismutase A enzymes) having particularly desirable properties (e.g., antioxidant properties). In certain embodiments the enzymes (e.g., SOD enzymes) are produced by, derived from or isolated from a lactic acid bacteria, such as *Lactococcus lactis* bacteria (e.g., from a *Lactococcus lactis* CNCM I-1631 bacterial strain).

In some embodiments the invention relates to a method of providing an antioxidant effect to a subject, comprising administering an effective amount of a composition to the subject, wherein the composition comprises a superoxide dismutase (SOD) enzyme or functional portion thereof obtained from a lactic acid bacterial strain (e.g., *Lactococcus lactis* such as *Lactococcus lactis* CNCM I-1631 bacterial strain) and is optionally isolated. The invention also relates to a composition comprising a superoxide dismutase (SOD) enzyme or functional portion thereof obtained from a lactic acid bacterial strain (e.g., *Lactococcus lactis*, such as the *Lactococcus lactis* CNCM I-1613 bacterial strain) and optionally isolated, for use in providing an antioxidant effect to a subject. The invention also relates to the use of a composition comprising a superoxide dismutase (SOD) enzyme or functional portion thereof obtained from a lactic acid bacterial strain (e.g., *Lactococcus lactis*, such as the *Lactococcus lactis* CNCM I-1613 bacterial strain) and optionally isolated, for the manufacture of a medicament (including functional foods) for use in providing an antioxidant effect to a subject.

In certain embodiments, the inventions relate to the use of a composition comprising a superoxide dismutase (SOD) enzyme or functional portion thereof obtained from a *Lactococcus lactis* bacterial strain for the manufacture of a medicament for reducing ROS-induced damage or treating an inflammatory condition in a subject in need thereof. For example, in some embodiments, the ROS-induced damage results from one or more conditions selected from the group consisting of inflammatory bowel disease, ulcerative colitis, diversion colitis, Crohn's disease, cancers of the gastrointestinal tract, irritable bowel syndrome, obesity and type II diabetes mellitus. In some embodiments, the *Lactococcus lactis* bacterial strain is CNCM I-1631. In some embodiments, the SOD enzyme is a superoxide dismutase A (SOD-A) enzyme or comprises an isolated polypeptide comprising SEQ ID NO: 1, SEQ ID NO: 2, SEQ ID NO: 3, or a functional portion thereof. In some embodiments the antioxidant effect involves reducing reactive oxygen species (ROS)-induced damage to the gastrointestinal tract of a subject, and the method comprises administering an effective amount of a composition to the subject and thereby reducing the ROS-induced damage, wherein the composition comprises an enzyme or functional portion thereof obtained from a lactic acid bacteria (e.g., *Lactococcus lactis* such as *Lactococcus lactis* CNCM I-1631 bacterial strain) and is optionally isolated.

In some embodiments the antioxidant effect involves reducing oxidative stress in a subject, and the method comprises administering an effective amount of a composition to the subject and thereby reducing the oxidative stress, wherein the composition comprises an enzyme or functional portion thereof obtained from a lactic acid bacteria (e.g., *Lactococcus lactis* such as *Lactococcus lactis* CNCM I-1631 bacterial strain) and is optionally isolated.

In some embodiments the enzyme is an antioxidant enzyme. In some embodiments the enzyme is superoxide dismutase (SOD). In some embodiments the enzyme is a superoxide dismutase A (SOD-A) enzyme. In some embodiments the enzyme comprises an isolated polypeptide comprising SEQ ID NO: 1 or a functional portion thereof. In some embodiments the SOD-A is encoded by a polynucleotide comprising SEQ ID NO: 2, or SEQ ID NO: 3, or a functional portion of either. In some embodiments the enzyme is isolated. In some embodiments the composition comprises at least one bacterial strain.

In some embodiments the subject is a mammal, such as a human. In some embodiments the composition is administered orally. In some embodiments the composition is selected from the group consisting of a food (e.g., a medical food or a functional food), a pharmaceutical and a dietary supplement.

In some embodiments the ROS-induced damage results from one or more conditions selected from the group consisting of inflammatory bowel disease, ulcerative colitis, diversion colitis, Crohn's disease, cancers of the gastrointestinal tract, irritable bowel syndrome, obesity and type II diabetes mellitus. In some embodiments the oxidative stress involves the tissues of the gastrointestinal tract of the subject. In some embodiments the oxidative stress is a result of one or more conditions selected from the group of conditions consisting of inflammatory bowel disease, ulcerative colitis, Crohn's disease, diversion colitis, pouchitis, aging, cancers of the gastrointestinal tract, irritable bowel syndrome, obesity and type II diabetes mellitus. In certain embodiments the oxidative stress arises in the course of intestinal inflammation, and in some embodiments the oxidative stress comprises reactive oxygen species (ROS)-induced damage to the tissues of the gastrointestinal tract.

The invention also relates to a method of identifying candidate therapeutic lactic acid bacteria, wherein the method comprises the steps of (a) screening lactic acid bacteria to identify candidate bacteria that express an enzyme; and (b) testing said candidate bacteria for at least one therapeutic property in an appropriate model to identify candidate therapeutic bacteria.

In some embodiments the enzyme is an antioxidant enzyme. In some embodiments the enzyme is a superoxide dismutase (SOD) enzyme. In some embodiments the enzyme is SOD-A.

In some embodiments the lactic acid bacteria of (a) are selected from the group consisting of *Lactococcus, Lactobacillus, Leuconostoc, Pediococcus* and *Streptococcus*. In some embodiments the lactic acid bacteria are *L. lactis*.

In some embodiments the at least one therapeutic property is one or more properties selected from the group consisting of ability to neutralize reactive oxygen species (ROS), ability to reduce ROS-induced damage, ability to reduce oxidative stress, antioxidant effect, ability to treat an inflammatory condition, and ability to treat an inflammatory bowel disease. In some embodiments the at least one therapeutic property is the ability to treat ulcerative colitis and the model is a TRUC murine model. In some embodiments the at least one therapeutic property is the ability to treat ulcerative colitis and the model is a IL10$^{-/-}$ murine model. In some embodiments the therapeutic lactic acid bacteria have properties similar to *L. lactis* CNCM I-1631 bacteria The invention also relates to an isolated bacterial strain expressing a superoxide dismutase (SOD) enzyme, or a functional portion thereof, isolated from a *Lactococcus lactis* CNCM I-1631 bacterial strain, wherein the isolated bacterial strain is not an *L. lactis* CNCM I-1631 bacterial strain. In some embodiments the SOD enzyme is SOD-A. In some embodiments the bacterial strain is a *L. lactis* bacterial strain. In some embodiments the strain is transfected with a plasmid comprising a polynucleotide encoding the SOD enzyme or a functional portion thereof (e.g., a plasmid encoding SOD-A isolated from a *L. lactis* CNCM I-1631 bacterial strain).

The invention also relates to an expression vector comprising a polynucleotide encoding a superoxide dismutase A (SOD-A) enzyme, or a functional portion thereof, from a *Lactococcus lactis* CNCM I-1631 bacterial strain. In some embodiments the vector is a virus or a plasmid.

The invention also relates to a method of treating a subject having an inflammatory condition, wherein the method comprises administering an effective amount of a composition to the subject and thereby treating the inflammatory condition, wherein the composition comprises an enzyme or functional portion thereof isolated from a lactic acid bacterial strain. In some embodiments the lactic acid bacterial strain is selected from the group consisting of *Lactobacillus, Leuconostoc, Pediococcus, Streptococcus* and *Lactococcus*. In some embodiments the lactic acid bacteria is *Lactococcus lactis*. In certain embodiments the lactic acid bacteria is *Lactococcus lactis* CNCM I-1631 bacteria.

In some embodiments the enzyme is an antioxidant enzyme. In some embodiments the enzyme is SOD, e.g., SOD-A. In some embodiments the inflammatory condition is induced by reactive oxygen species (ROS).

In some embodiments the composition comprises a bacterial strain which does not naturally (natively) produce the enzyme and has been engineered to express the enzyme.

In certain embodiments the at least one bacteria naturally (natively) produces an antioxidant enzyme. In certain embodiments the at least one bacteria is engineered to express an antioxidant enzyme (e.g., a SOD enzyme such as SOD-A) or a functional portion thereof (e.g., a functional portion of such enzyme encoded by a polynucleotide sequence comprising SEQ ID NO: 3). In certain embodiments the at least one bacteria naturally produces an antioxidant enzyme and is engineered to produce an antioxidant enzyme (e.g., engineered to produce additional quantities of the same enzyme or portions thereof or to produce one or more additional different enzymes or portions). The composition can also comprise mixtures of bacteria, e.g., mixtures of different bacterial genera, mixtures of different bacterial species, mixtures of naturally-occurring and engineered bacteria, etc.

For example, the bacteria (e.g., lactic acid bacteria) can comprise one or more genetic modifications that result in the overexpression of an antioxidant enzyme (e.g., SOD-A) relative to a native, wild-type or otherwise unmodified strain of such bacteria. The bacteria can be, for example, lactic acid bacteria selected from the group consisting of *Lactobacillus, Leuconostoc, Pediococcus, Streptococcus* and *Lactococcus*.

In some embodiments the composition comprises lactic acid bacteria (e.g., *L. lactis* CNCM I-1631 bacterial strain)

as well as one or more isolated enzymes (e.g., antioxidant enzymes) or portions thereof.

The above discussed and many other features and attendant advantages of the present invention will become better understood by reference to the following detailed description of the invention when taken in conjunction with the accompanying examples.

BRIEF DESCRIPTION OF THE DRAWINGS

FIG. 9 illustrates the amino acid sequence of the superoxide dismutase A (SOD-A) enzyme isolated from the Lactococcus lactis CNCM I-1631 bacterial strain (SEQ ID NO: 1).

FIG. 10 illustrates a portion of the polynucleotide sequence of the superoxide dismutase (SOD-A) enzyme comprising the coding region isolated from the Lactococcus lactis CNCM I-1631 bacterial strain (SEQ ID NO: 2).

FIG. 11 illustrates a polynucleotide sequence encoding a functional portion of the superoxide dismutase A (SOD-A) enzyme isolated from the Lactococcus lactis CNCM I-1631 bacterial strain (SEQ ID NO: 7).

DETAILED DESCRIPTION OF THE INVENTION

Figure 1:
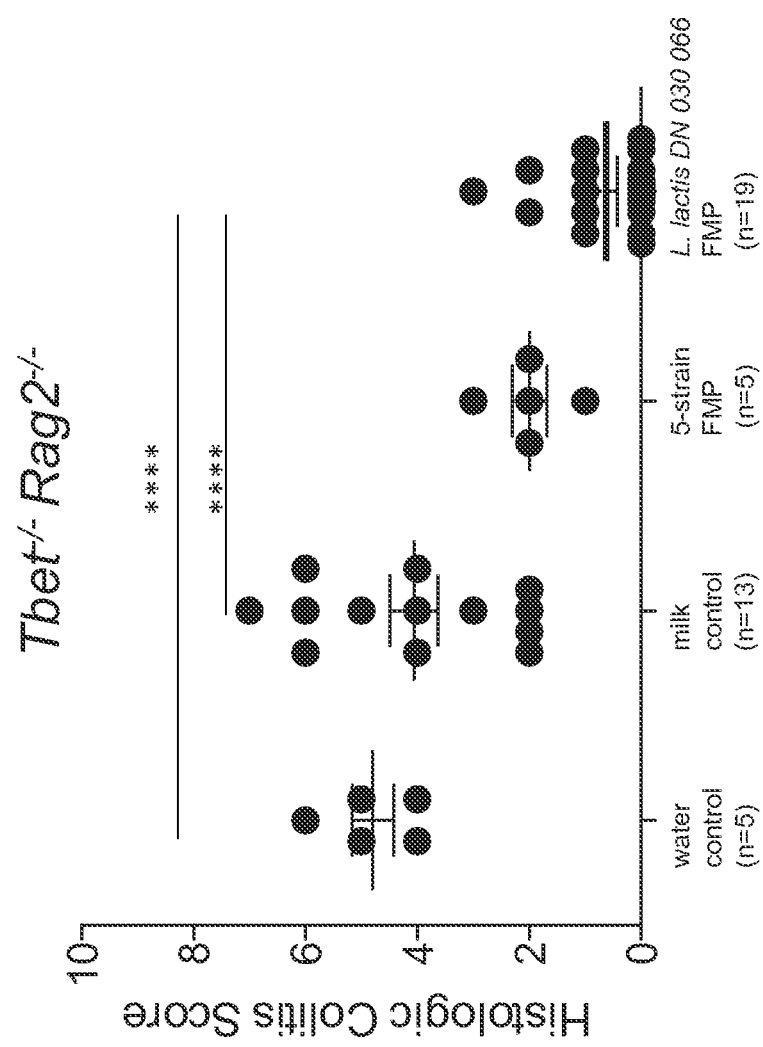
FIG. 1 illustrates histologic colitis scores for T-bet$^{-/-}$ Rag2$^{-/-}$ (TRUC) mice administered either a water control, a milk control, a five strain fermented milk product that contains the Lactococcus lactis CNCM I-1631 bacterial strain or a Lactococcus lactis CNCM I-1631 bacterial strain fermented milk product. Products were administered for four weeks. A one-way ANOVA with Dunn's post-hoc test was performed to evaluate statistical significance, **** indicates the p-value<0.0001.

The inventions described herein are generally directed to novel compositions (e.g., therapeutic or preventative compositions) and related methods of conferring an antioxidant effect on a subject and/or treating inflammatory conditions such as inflammatory bowel disease. Provided are novel therapies for the treatment of inflammatory bowel disease and suppression of the symptoms that characterize inflammatory bowel disease. In particular the present inventions provide means of conferring an antioxidant effect such as reducing, mitigating or otherwise neutralizing the damaging effects of reactive oxygen species (ROS), particularly in the gastrointestinal tract, and/or reducing or otherwise neutralizing oxidative stress, and the damaging effects that such stress exerts, for example, on the cells and tissues of the gastrointestinal tract.

As is used herein, the phrase "inflammatory condition" generally refers to any disease, disorder or pathological condition involving inflammation or otherwise having an inflammatory component (e.g., an inflammatory response that a subject develops as a result of exposure to injury or insult or pathology). Exemplary inflammatory conditions include inflammatory bowel disease, ulcerative colitis, Crohn's disease, diversion colitis, pouchitis, aging, irritable bowel syndrome, and cancer of the gastrointestinal tract, obesity and type II diabetes; these diseases manifest signs of oxidative stress and ROS-induced damage.

As used herein, the phrase "inflammatory bowel disease" broadly refers to a set of chronic, idiopathic, immune-mediated disorders that result in the inflammation of the gastrointestinal tract, and such phrase collectively includes each of ulcerative colitis, Crohn's disease, irritable bowel syndrome, diversion colitis, cancers of the gastrointestinal tract, and pouchitis.

While the underlying cause of inflammatory bowel disease has not yet been fully elucidated, it appears that ROS plays a role in the inflammatory processes and that such ROS exert damaging effects on the cells and tissues of the gastrointestinal tract. As used herein, the terms "reactive oxygen species" and "ROS" generally refer to the free radical forms of oxygen or oxygen-containing compounds such as hydrogen peroxide and superoxide. ROS are chemically reactive, metabolic by-products that may accumulate in the gastrointestinal tracts of subjects with inflammatory bowel disease. Accumulating ROS, such as superoxide and hydrogen peroxide, are capable of promoting DNA damage by oxidizing DNA bases and generating DNA adducts at a rate that outpaces DNA repair mechanisms, further contributing to the inflammation that characterizes inflammatory bowel diseases (Garrett et al. *Cancer Cell* 16: 208-219 (2009)).

Accumulating ROS increase the oxidative stress to which an affected subject, and in particular such subject's cells and cellular structures, is exposed. As used herein, the phrase "oxidative stress" broadly refers to a condition (e.g., a condition that may be induced by the immune and/or environmental stressors to which a subject may be exposed) which causes ROS levels to increase beyond the subject's natural antioxidant capacities. Therefore, oxidative stress is characterized by an imbalance of oxidative and anti-oxidative reactions, where such imbalance is shifted in the direction of an oxidative state, thereby resulting in oxidative damage. Such imbalance results in an accumulation of ROS, which in turn may promote an inflammatory state and result in damage to cellular structures. Conditions in which subjects may be under oxidative stress or at risk for developing oxidative stress include inflammatory bowel disease, aging, irritable bowel syndrome, cancers of the gastrointestinal tract, obesity and diabetes mellitus (e.g., type II diabetes).

As described herein, certain enzymes (e.g., antioxidant enzymes such as superoxide dismutase (SOD) enzymes), produced by lactic acid bacteria (e.g., *Lactococcus lactis* bacterial strains), may be used to treat or prevent certain pathological conditions including inflammatory bowel disease. Without wishing to be bound by theory, it is believed that the enzymes reduce or otherwise neutralize ROS and thereby treat or prevent pathological conditions that may in part result from the oxidative effects caused by accumulating ROS (e.g., inflammatory bowel disease).

Lactic acid bacteria are Gram-positive, rod-shaped bacilli or cocci that produce lactic acid as the major metabolic end-product of carbohydrate fermentation. Exemplary lactic acid bacteria include *Lactobacillus, Leuconostoc, Pediococcus, Streptococcus* and *Lactococcus*. In certain embodiments, the present invention relates to enzymes (e.g., enzymes having antioxidant properties) that are produced by, derived from or isolated from lactic acid bacteria, as well as to functional portions of these enzymes, polynucleotides encoding these enzymes and portions, cells comprising the polynucleotides or producing the enzymes or portions (either naturally/natively, or as a result of genetic engineering to cause bacterial strains which do not natively produce the enzyme(s) to produce the enzyme(s), or as a result of genetic engineering to cause bacterial strains to produce increased amounts of the enzyme(s) compared with corresponding native strains), and uses thereof.

In certain embodiments, the lactic acid bacteria comprise a *Lactococcus* bacterial strain (e.g., *L. lactis*). One such bacterial strain, which is referred to herein as the "*L. lactis* CNCM I-1631 bacterial strain" or the "*L. lactis* DN 030 066 strain," has been disclosed in International Publication No. WO/1997/016529, the entire contents of which are incorporated by reference herein. The *L. lactis* CNCM I-1631 bacterial strain, which is a Gram-positive, predominantly diplococci microorganism, has been deposited under the terms and conditions of the Budapest Treaty at the Collection Nationale de Cultures de Microorganisms on Oct. 24, 1995, under Accession number 1-1631.

As described herein, the *L. lactis* CNCM I-1631 bacterial strain is effective in a murine model of ulcerative colitis to reduce the colitis score in this model in a SOD-A-dependent manner. This strain is capable of reducing or otherwise neutralizing ROS and thereby treating conditions that may have as a feature thereof, or that may be complicated by oxidative stress (e.g., inflammatory bowel disease, irritable bowel syndrome, cancers of the gastrointestinal tract, type II diabetes, aging and/or obesity,). Accordingly, in certain embodiments the present inventions relate to compositions comprising an enzyme (e.g., the SOD-A enzyme) isolated from the *L. lactis* CNCM I-1631 bacterial strain and to related methods of using such compositions to treat oxidative stress. For example, the compositions and related methods disclosed herein are useful for the treatment of oxidative stress that is induced in a subject in response to an acute or chronic inflammatory condition or in response to the commensal bacterial species that populate the gastrointestinal tract of the subject. In certain embodiments, the isolated enzyme (e.g., an antioxidant enzyme, such as a SOD-A enzyme) may be used to reduce redox stress in the tissues of the gastrointestinal tract or to maintain or promote the homeostasis of the gastrointestinal tract. Yet in other embodiments, the isolated enzyme (e.g., SOD-A enzymes) and compositions (e.g., bacteria) comprising such enzymes may be administered to provide an antioxidant effect to a subject in need thereof (e.g., subjects having or otherwise afflicted with an inflammatory condition induced by the presence or accumulation of ROS).

Also disclosed herein are enzymes or functional portions thereof (e.g., enzymes isolated from lactic acid bacteria) that are characterized as having antioxidant properties. As used herein, the phrase "antioxidant enzyme" refers to an enzyme or functional portions thereof that have antioxidant properties or are otherwise capable of slowing, retarding or inhibiting oxidation or oxidative stress. In certain embodiments, such antioxidant enzymes are isolated from lactic acid bacteria (e.g., *L. lactis*). In certain embodiments, such antioxidant enzymes are isolated from an *L. lactis* CNCM I-1631 bacterial strain. Exemplary antioxidant enzymes may be, for example, superoxide dismutase (SOD).

As used herein to describe a cell or an enzyme (e.g., a SOD enzyme or a SOD-A enzyme), the term "isolated" generally means having been removed or separated from the native environment. For example, an isolated SOD-A enzyme may be separated from a *L. lactis* bacterial stain which expresses or produces (e.g., natively/naturally) the enzyme.

As used herein, the phrase "antioxidant effect" generally refers to the ability of a compound or composition (e.g., a composition comprising SOD-A) to reduce, slow, retard or otherwise inhibit oxidative stress (e.g., reduce or inhibit ROS-induced oxidative damage to cellular components such as DNA).

The compositions of the present invention may be used to treat or reduce ROS-induced damage (e.g., ROS-induced damage to the gastrointestinal tract of a subject). For example, disclosed herein are methods of treatment that comprise the administration of a composition comprising an antioxidant enzyme (e.g., SOD such as SOD-A) from (e.g., produced by or isolated from) a *L. lactis* CNCM I-1631 bacterial strain to a subject in need thereof. Such compositions may comprise one or more bacteria (e.g., bacteria which have been engineered or genetically-modified such that they express the SOD enzyme or that result in the overexpression of an antioxidant enzyme).

Also provided herein are isolated cells that have been modified (e.g., genetically modified) such that they produce one or more antioxidant enzymes or increased amounts of said one or more enzymes (e.g., SOD such as SOD-A) that are produced by the *L. lactis* CNCM I-1631 bacterial strain. For example, an isolated cell (e.g., a bacterial cell) may be transfected with a plasmid comprising a polynucleotide encoding the enzyme or functional portion thereof. Preferably the cell will be one which does not naturally produce the enzyme (e.g., if the SOD enzyme is derived from *L. lactis* CNCM I-1631 the genetically modified strain is not *L. lactis* CNCM I-1631). However in certain embodiments the cell naturally expresses the enzyme and the genetic modification results in overproduction of the enzyme. Following the integration and expression of such nucleic acids into the genome of the isolated cell, such cell will produce or secrete an antioxidant enzyme (e.g., a SOD-A enzyme from a *L. lactis* CNCM I-1631 bacterial strain). Such antioxidant enzyme may be isolated (e.g., harvested) from the culture medium and administered to a subject in accordance with the teachings of the present invention to reduce or treat oxidative stress or inflammatory conditions. Alternatively, the culture medium or the bacterial cell itself can be administered to the subject. In certain embodiments, the isolated cells comprise one or more genetic modifications that result in the overexpression of an antioxidant enzyme (e.g., relative to the unmodified cell). For example, one or more isolated cells that natively produce an antioxidant enzyme (e.g., SOD-A) may be genetically modified such that the amount of such produced antioxidant enzyme is increased (e.g., increased by 2-, 3-, 4-, 5-, 6-, 7-, 8-, 9-, 10-fold, or more).

A polynucleotide sequence encoding the SOD-A enzyme from *L. lactis* CNCM I-1631 is shown in SEQ ID NO: 2 (FIG. 10). Functional portions of the SOD-A enzyme (or other enzymes disclosed herein) can be identified using methods known in the art. For example, portions of the enzyme can be made using standard methods and tested for a property of interest (e.g., the ability to treat ulcerative colitis in a murine model, the ability to reduce or neutralize ROS, etc.). As used herein, a "functional portion" of an enzyme is one which shares one or more functional properties with the parent (intact) enzyme. In certain embodiments, the functional portion of the enzyme is a functional portion of a SOD-A enzyme encoded by a polynucleotide sequence of *Lactococcus lactis* CNCM I-1631 comprising SEQ ID NO: 3. Preferably the shared property or properties are those which relate to the methods described herein, such as the ability to neutralize reactive oxygen species (ROS), the ability to reduce ROS-induced damage, the ability to reduce oxidative stress, an antioxidant effect, the ability to treat an inflammatory condition, and/or the ability to treat an inflammatory bowel disease.

Also provided herein are expression vectors that can be used to genetically modify one or more isolated cells (e.g., bacterial cells). The genetically modified cells and their expression products (e.g., SOD-A enzyme or a functional portion thereof) may be used in accordance with the teachings of the present inventions. In certain embodiments, the expression vectors comprise a polynucleotide encoding an enzyme or functional portion thereof (e.g., SOD, SOD-A, or portion thereof) from a lactic acid bacteria. In certain embodiments, such expression vectors comprise a polynucleotide encoding an enzyme or functional portion there of (e.g., SOD, SOD-A, or portion thereof) from the *L. lactis* CNCM I-1631 bacterial strain. Such expression vectors may be, for example, a virus, plasmid, etc. as known in the art.

In certain aspects, the methods of the present invention comprise the administration of an effective amount of one or more enzymes (e.g., SOD-A enzyme, such as that isolated from the *L. lactis* CNCM I-1631 bacterial strain) to a subject having a disease or condition in which oxidative stress is implicated (e.g., an inflammatory condition such as ulcerative colitis). The amino acid sequence of the SOD-A enzyme of *L. lactis* CNCM I-1631 is provided herein as SEQ ID NO: 1 (FIG. 9). As used herein, the term "subject" means any mammal, including humans. In certain embodiments of the present invention the subject is an adult or an adolescent.

As used herein, the phrase "effective amount" means an amount sufficient to achieve a meaningful benefit (e.g., neutralizing damaging ROS or reducing the symptoms of inflammatory bowel disease). An effective amount of the enzymes (e.g., SOD-A enzymes) in the compositions of the present invention may be generally determined based on the ability of such enzymes to exert an antioxidant effect. Generally, the amount of enzyme (e.g., a SOD, SOD-A enzyme) administered to a subject will depend upon the characteristics of the subject and the severity of the subject's oxidative stress, disease or inflammatory condition. In certain embodiments, the compositions may be administered to a subject (e.g., administered orally) once daily, twice daily, three times daily, four times daily, five times daily, six times daily, seven times daily, eight times daily, or more.

The compositions of the present invention can be administered to a subject by any suitable routes of administration. Preferably, following the administration of such compositions a therapeutic concentration of the enzyme (e.g., a SOD or SOD-A enzyme) is achieved and/or maintained in the tissues of the gastrointestinal tract (e.g., within the lumen of the gastrointestinal tract). In certain embodiments, the composition is combined with suitable excipients and formulated for enteral or rectal administration. Alternatively, in certain embodiments, the compositions of the present invention may be prepared for parenteral administration. General techniques applicable to the formulation and administration of the compositions of the present invention may be found in "Remington's Pharmaceutical Sciences," Mack Publishing Co., Easton, Pa., latest edition. The compositions of the present invention can also be administered or co-administered as part of a therapeutic regimen with other suitable therapeutic or prophylactic agents (e.g., administered concurrently or sequentially).

In embodiments where the compositions are administered to a subject orally, such compositions may be prepared or formulated as a food (e.g., a dairy product, preferably a fermented dairy product such as yogurt) or as a functional food (e.g., a nutritional supplement). In other embodiments, such compositions may be prepared or formulated, for example, as a pharmaceutical, a dietary supplement and/or a medical food. In one embodiment a fermented dairy product can be obtained by fermentation of a medium, preferably a milk, by a *L. lactis* CNCM I-1631 bacterial strain and optionally further strains, such as, for example, a mixture of *L. Bugaricus* and *S. thermophilus* strains.

The invention provides methods of identifying additional candidate therapeutic lactic acid bacteria, as well as identifying and isolating the beneficial antioxidant enzymes (e.g., SOD enzymes) of those bacteria.

For example, the skilled artisan can readily screen lactic acid bacteria to identify candidate bacteria that express an antioxidant enzyme and then test those candidate bacteria for at least one therapeutic property in an appropriate model to identify additional candidate therapeutic bacteria. Once such bacteria are identified, the antioxidant enzyme(s) can be isolated and tested for similar therapeutic properties as described herein and as readily known to the skilled artisan. Additional bacteria and SOD genes identified by these methods can be used in methods (e.g., methods of treatment) as described herein.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The entire contents of all of the references (including literature references, issued patents and published patent applications and websites) cited throughout this application are hereby expressly incorporated by reference.

The embodiments described herein will be further illustrated by the following Examples, which should not be construed as limiting.

EXAMPLE 1

The TRUC (T-bet$^{-/-}$×RAG2$^{-/-}$) murine model represents a suitable model to evaluate the ability of the present inventions to mitigate or otherwise treat inflammatory bowel disease. TRUC mice develop a spontaneous, highly penetrant, aggressive, commensal-dependent ulcerative colitis characterized by a dysfunction and loss of epithelial barrier integrity, which results from T-bet deficiency in the innate immune system (Garrett, et al. *Cell* 131(1): 33-45 (2007); Garret, et al. *Cytokine* 48(1-2):144-147(2009)). TRUC mice therefore provide a useful model for evaluating the ability of the *Lactococcus lactis* CNCM I-1631 bacterial strain to ameliorate the colitis induced in such TRUC mice and to evaluate efficacy of the present inventions.

The present study was conducted by treating the TRUC mice for 4 weeks with either a water control (n=5), a milk control (n=13), a five strain fermented milk product that contains the *Lactococcus lactis* CNCM I-1631 bacterial strain (n=5), or a *Lactococcus lactis* CNCM I-1631 bacterial strain fermented milk product (n=19). In each case the controls and the fermented milk products that contained the *L. lactis* bacteria were delivered by gentle oral instillation to the mice.

After treatment for 4 weeks the mice were sacrificed and their colons removed and dissected free from the anus to distal to the cecum, colonic contents removed, and colons cleaned with PBS prior to fixation in 4% PFA or 10% neutral buffered formalin followed by routine paraffin embedding. After paraffin embedding, 0.5 micrometer sections were cut, stained and examined. Colitis was assessed based on an assigned histological colitis score.

As illustrated in FIG. 1, administration of the fermented milk products that contained the *L. lactis* CNCM I-1631 bacterial strain ameliorated the colitis induced in the treated TRUC mice, as evidenced by histologic evaluation. In contrast, the administration of each of the water and milk controls failed to ameliorate the induced colitis. The foregoing suggests that the *L. lactis* CNCM I-1631 bacterial strain is capable of improving or otherwise ameliorating colitis in this TRUC mouse model.

EXAMPLE 2

The present inventors also evaluated the ability of the *Lactococcus lactis* CNCM I-1631 bacterial strain to affect histologic colitis scores in an interleukin 10 knockout (I110$^{-/-}$) mouse model of colitis that resembles many aspects of human inflammatory bowel disease.

The I110$^{-/-}$ mice were administered either a water control (n=8), a milk control (n=8), or a *Lactococcus lactis* CNCM I-1631 bacterial strain fermented milk product (n=9) for four weeks. In each case the controls and the fermented milk products that contained the *L. lactis* bacteria were delivered by gentle oral instillation to the mice.

After treatment for 4 weeks the I110$^{-/-}$ mice were sacrificed and their colons removed and dissected free from the anus to distal to the cecum, colonic contents removed, and colons cleaned with PBS prior to fixation in 4% PFA or 10% neutral buffered formalin followed by routine paraffin embedding. After paraffin embedding, 0.5 micrometer sections were cut, stained and examined. Colitis was assessed based on an assigned histological colitis score.

Figure 2:
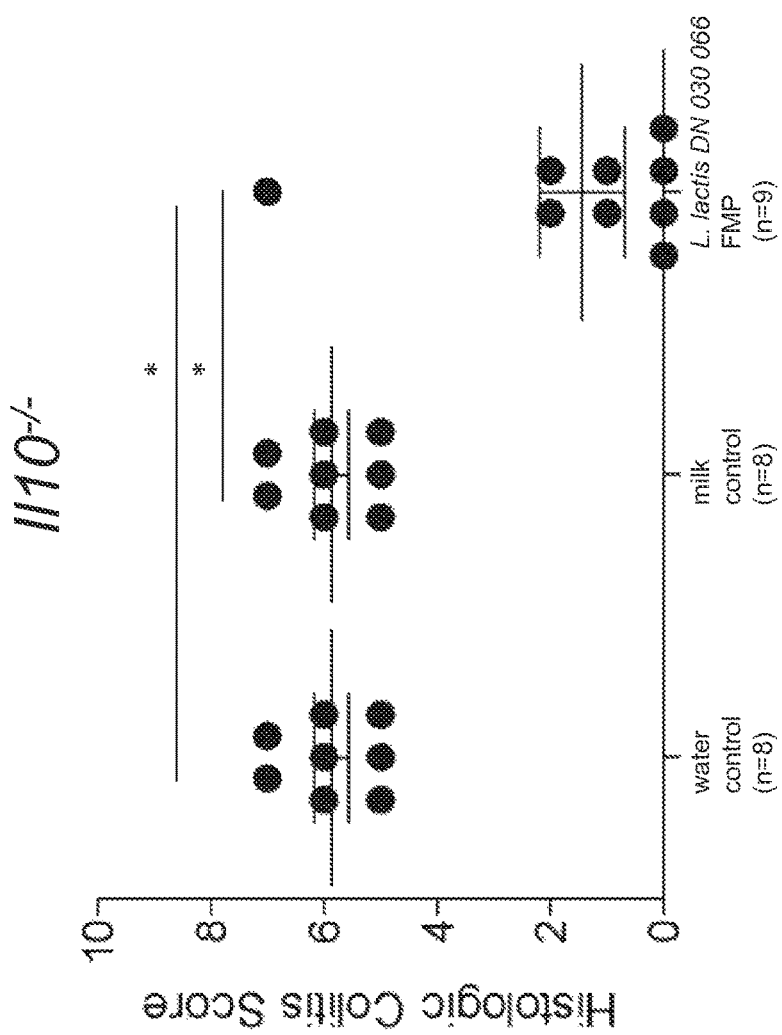
FIG. 2 illustrates histologic colitis scores for Il10$^{-/-}$ mice administered either a water control, a milk control, or a Lactococcus lactis CNCM I-1631 bacterial strain fermented milk product (FMP). Products were administered for four weeks. A one-way ANOVA with Dunn's post-hoc test was performed to evaluate statistical significance, * indicates the p-value<0.05.

As illustrated in FIG. 2, administration of the fermented milk product that contained the *L. lactis* CNCM I-1631 bacterial strain ameliorated the colitis induced in the I110$^{-/-}$ mice, as evidenced by histologic colitis score. In contrast, the administration of each of the water and milk controls failed to ameliorate the colitis induced in the I110$^{-/-}$ mice, as also evidenced by histologic colitis score. The foregoing results therefore demonstrate that the *L. lactis* CNCM I-1631 bacterial strain is capable of improving or otherwise ameliorating colitis in the I110$^{-/-}$ mouse model.

EXAMPLE 3

The administration of dextran sodium sulfate results in epithelial damage and a robust inflammatory response in the colon that lasts several days and is an established murine inflammatory injury model of acute colitis. The present study was performed to evaluate the ability of the *Lactococcus lactis* CNCM I-1631 bacterial strain to affect histologic colitis scores in wild-type mice administered dextran sodium sulfate for 5 days.

Wild-type mice were treated with dextran sodium sulfate (experimental day 3 through 8) and were administered either a water control (n=8), a milk control (n=8) or a *Lactococcus lactis* CNCM I-1631 bacterial strain fermented milk product (n=9) from experimental day 1 through 10.

After treatment for 10 days, the dextran sodium sulfate-treated mice were sacrificed and their colons removed and dissected free from the anus to distal to the cecum, colonic contents removed, and colons cleaned with PBS prior to fixation in 4% PFA or 10% neutral buffered formalin followed by routine paraffin embedding. After paraffin embedding, 0.5 micrometer sections were cut, stained and examined. Colitis was assessed based on an assigned histological colitis score.

Figure 3:
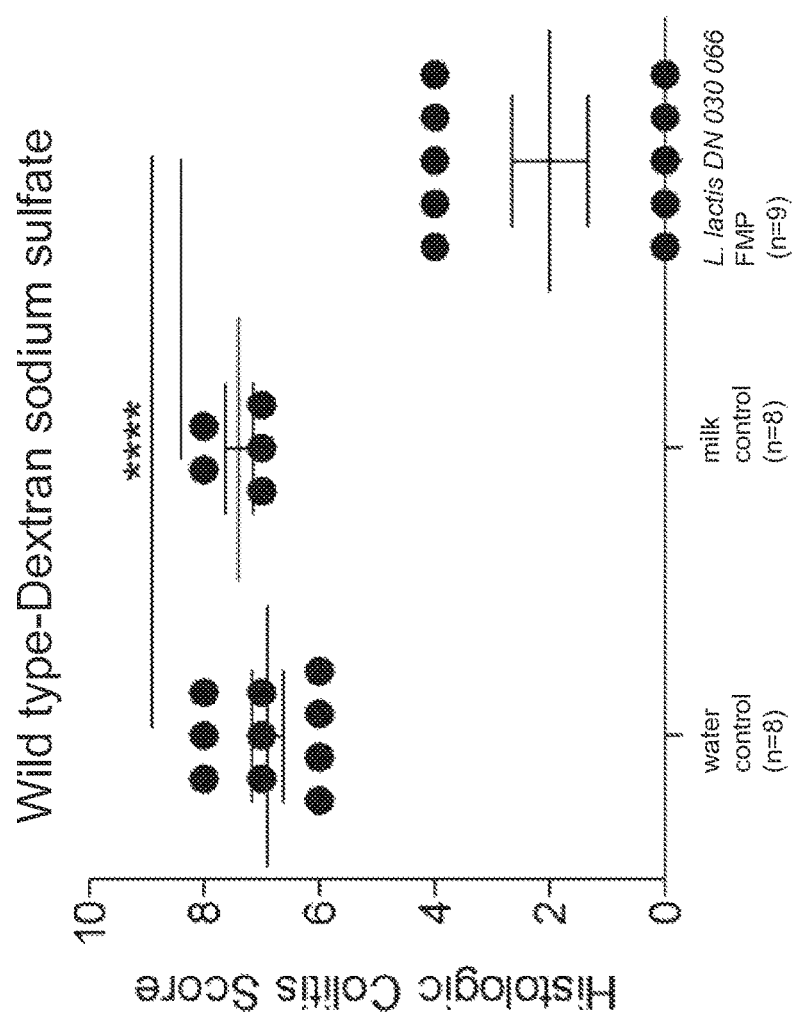
FIG. 3 illustrates histologic colitis scores for wild type mice treated with dextran sodium sulfate for 5 days (experimental day 3 through 8) and administered either a water control, a milk control, or a Lactococcus lactis CNCM I-1631 bacterial strain fermented milk product from experimental day 1-10. A one-way ANOVA with Dunn's post-hoc test was performed to evaluate statistical significance, * indicates the p-value<0.0001.

As illustrated in FIG. 3, administration of the *Lactococcus lactis* CNCM I-1631 bacterial strain fermented milk product ameliorated the colitis induced in the dextran sodium sulfate-treated mice, as evidenced by histologic colitis score. In contrast, the administration of each of the water and milk controls failed to ameliorate the colitis induced in the dextran sodium sulfate-treated mice, as also evidenced by histologic colitis score. The foregoing results further demonstrate that the *L. lactis* CNCM I-1631 bacterial strain is capable of improving or otherwise ameliorating colitis in the wild-type mice treated with dextran sodium sulfate.

EXAMPLE 4

Figure 4:
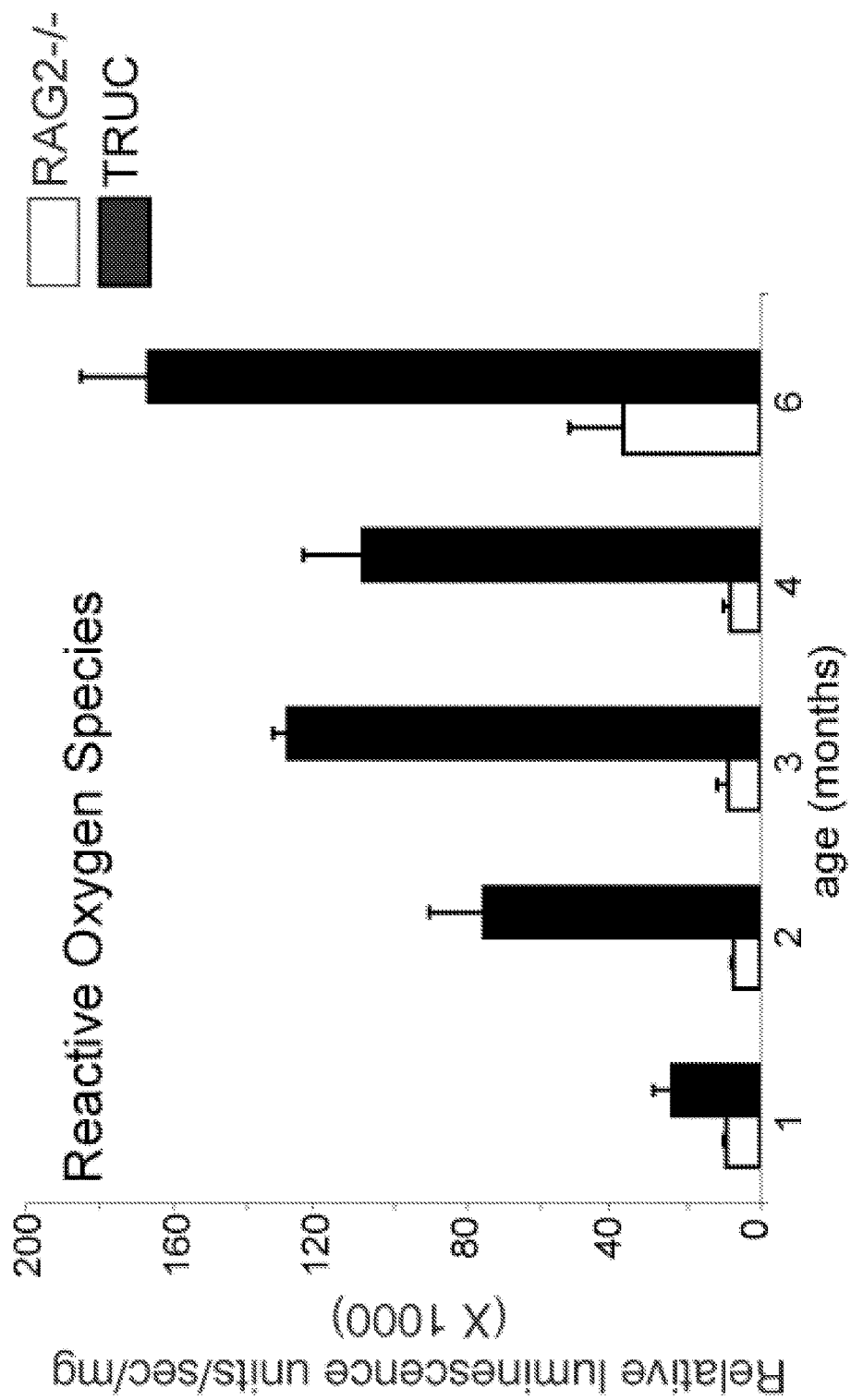
FIG. 4 illustrates that reactive oxygen species are elevated in the distal colons of the TRUC murine model of ulcerative colitis relative to control RAG2$^{-/-}$ mice. Open bars represent the control RAG2$^{-/-}$ mice and the shaded bars represent TRUC mice (five to eight mice per group). Means are graphed; error bars represent ±SD, p<0.001 for all comparison between TRUC 1 month and TRUC 2-6 months.
Figure 5:
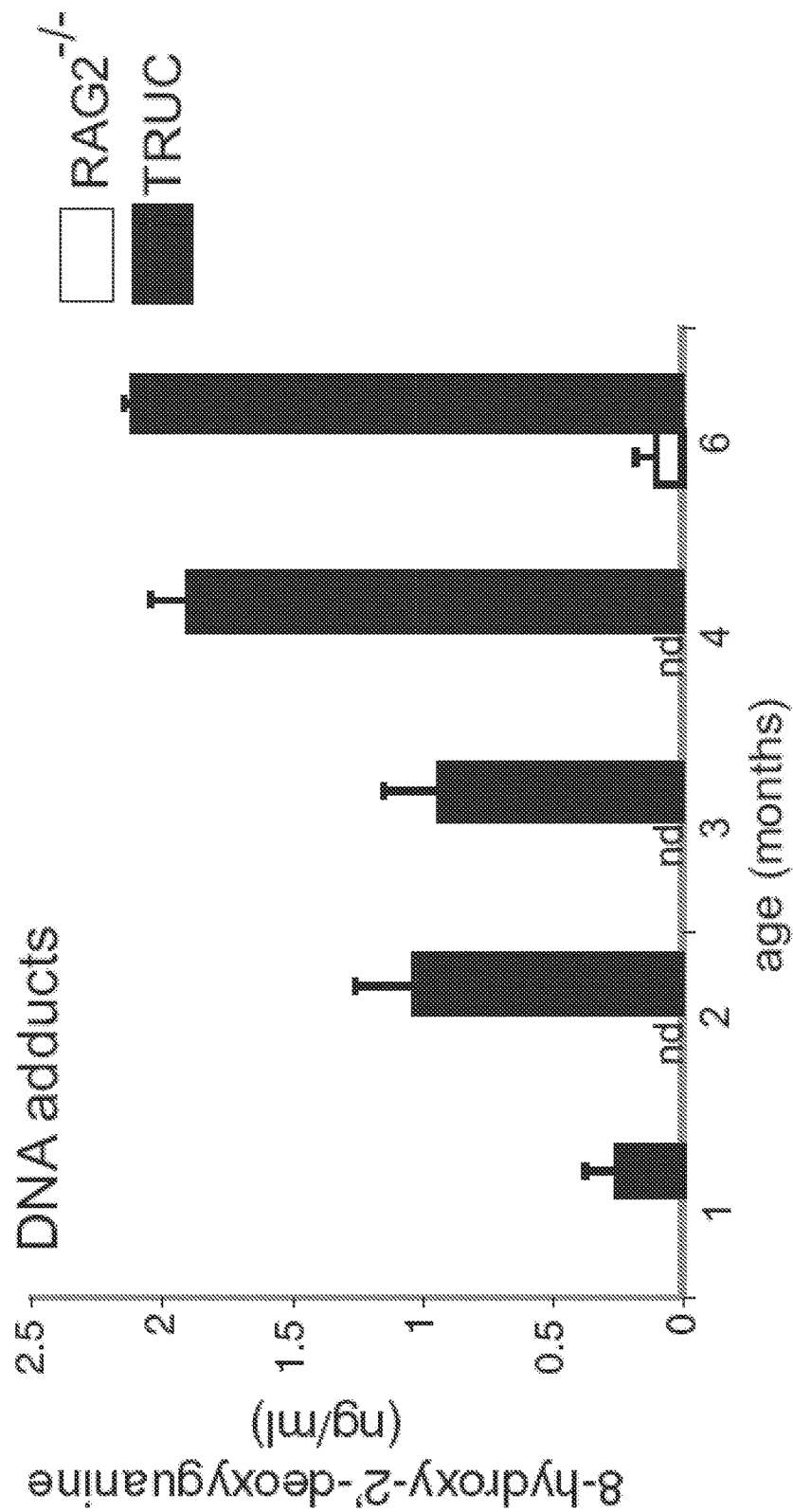
FIG. 5 demonstrates that DNA adducts, and in particular the reactive oxygen species-induced 8-hydroxy-2'-deoxyguanine DNA adduct, are markedly increased in the TRUC murine model of ulcerative colitis relative to the control RAG2$^{-/-}$ mice. Open bars represent the control RAG2$^{-/-}$ mice and the shaded bars represent TRUC mice (six to nine mice per group). Means are graphed; error bars represent ±SD, p<0.001 for all comparison between TRUC 1 month and TRUC 2-6 months.

The TRUC (T-bet$^{-/-}$×RAG2$^{-/-}$) murine model also represents a suitable model to evaluate the ability of the present inventions to reduce damaging reactive oxygen species. As illustrated in FIG. 4, the distal colons of the TRUC mice are rich in reactive oxygen species relative to the distal colons of RAG2$^{-/-}$ mice. As shown in FIG. 5, the presence of DNA adducts as measured by levels of 8-hydroxy-2-deoxyguanine were an untoward consequence of the reactive oxygen species measured in the TRUC mice and the levels of these adducts increased 3-fold between 1 and 2 months in TRUC mice and were highest in 4 and 6 month old TRUC mice (Garrett et al., *Cancer Cell* 16: 208-219 (2009)). TRUC mice therefore provide a useful model for evaluating the ability of the present inventions to reduce or otherwise neutralize reactive oxygen species.

To evaluate the ability of the present inventions to affect superoxide levels in primary colonic epithelial cells, primary colonic epithelial cells were incubated with either a control media, the *Lactococcus lactis* CNCM I-1631 bacterial strain, or a *Lactococcus lactis* CNCM I-1631 bacterial strain deficient in SOD-A. Xanthine-xanthine oxide was used to stimulate epithelial superoxide levels, dihydroethidium bromide was used to stain cells for the detection of superoxide levels, and cells were analyzed and mean fluorescence intensity was calculated using flow cytometry.

Figure 6:
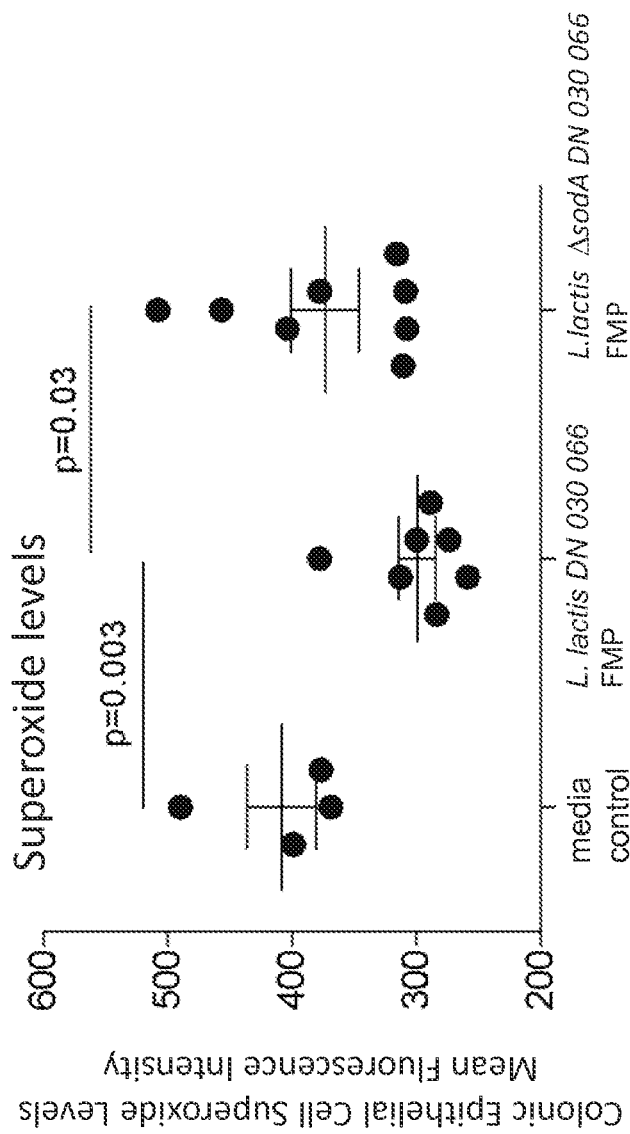
FIG. 6 demonstrates that superoxide levels of primary colonic epithelial cells incubated with media, the Lactococcus lactis CNCM I-1631 bacterial strain fermented milk product or Lactococcus lactis CNCM I-1631 bacterial strain deficient in SOD-A. Xanthine-xanthine oxide was used to stimulate epithelial superoxide levels, dihydroethidium bromide was used to stain cells for the detection of superoxide levels, and cells were analyzed and mean fluorescence intensity was calculated using flow cytometry. Each symbol represents epithelial cells obtained from 2-4 mice. P-values are shown with horizontal lines indicated the groups being compared, Kruskall-Wallis test.

As illustrated in FIG. 6, administration of the fermented milk products that contained the *L. lactis* CNCM I-1631 bacterial strain reduced superoxide levels in colonic epithelial cells relative to both the control media and the *Lactococcus lactis* CNCM I-1631 bacterial strain deficient in SOD-A, as evidenced by a reduction in mean fluorescence intensity. The foregoing thus suggests that the *L. lactis* CNCM I-1631 bacterial strain is capable of reducing superoxide levels in colonic epithelial cells in a SOD-A dependent fashion.

EXAMPLE 5

In an effort to further demonstrate that the *L. lactis* CNCM I-1631 bacterial strain improves colitis in a SOD-A dependent manner, a further study was performed to demonstrate the ability of the *Lactococcus lactis* CNCM I-1631 bacterial strain to affect histologic colitis scores in TRUC (T-bet$^{-/-}$ Rag2$^{-/-}$) mice.

TRUC mice were administered a wild-type *Lactococcus lactis* CNCM I-1631 bacterial strain fermented milk product (n=9), a *Lactococcus lactis* CNCM I-1631 bacterial strain with a deleted genomic SOD-A gene fermented milk product (n=20), or a *Lactococcus lactis* CNCM I-1631 bacterial strain with a deleted genomic SOD-A gene with expression complemented with a plasmid expressing SOD-A fermented milk product (n=12). After treatment for 4 weeks the mice were sacrificed and their colons removed and dissected free from the anus to distal to the cecum, colonic contents removed, and colons cleaned with PBS prior to fixation in 4% PFA or 10% neutral buffered formalin followed by routine paraffin embedding. After paraffin embedding, 0.5 micrometer sections were cut, stained and examined. Colitis was assessed based on an assigned histological colitis score.

Figure 7:
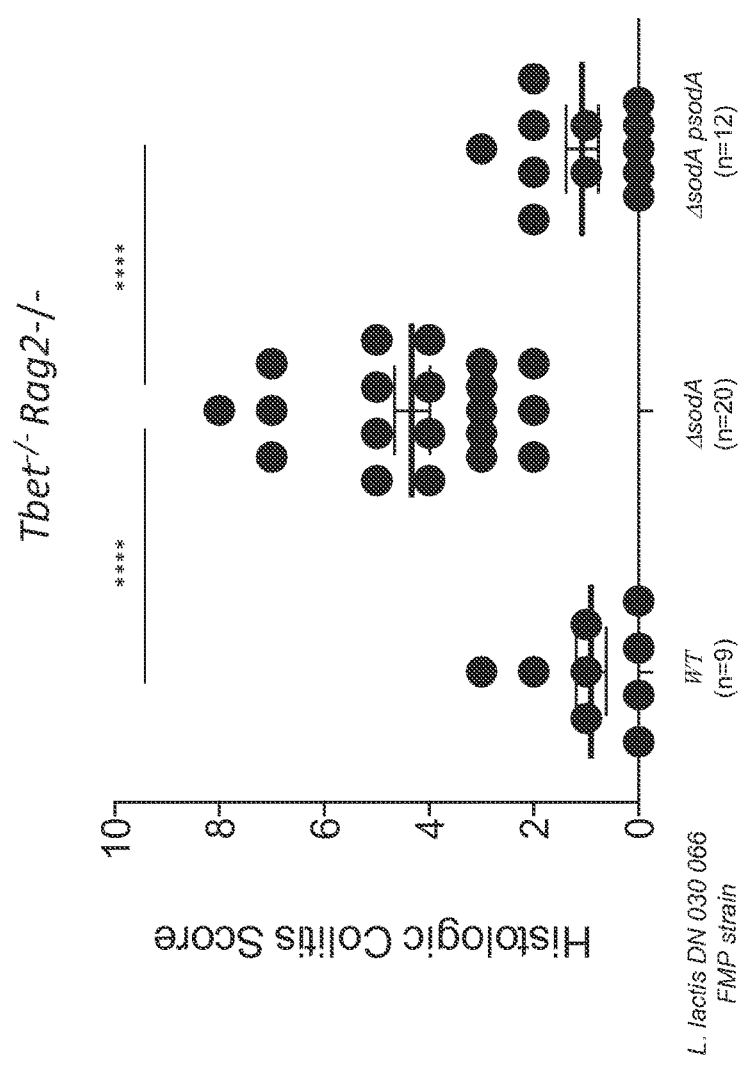
FIG. 7 illustrates histologic colitis scores for T-bet$^{-/-}$ Rag2$^{-/-}$ mice administered either a Lactococcus lactis CNCM I-1631 bacterial strain fermented milk product for four weeks, a Lactococcus lactis CNCM I-1631 bacterial strain with a deleted genomic SOD-A gene fermented milk product for four weeks, or a Lactococcus lactis CNCM I-1631 bacterial strain with a deleted genomic SOD-A gene with expression complemented with a plasmid expressing SOD-A fermented milk product for four weeks. A one-way ANOVA with Dunn's post-hoc test was performed to evaluate statistical significance, **** indicates the p-value<0.0001.

As illustrated in FIG. 7, administration of the wild-type *Lactococcus lactis* CNCM I-1631 bacterial strain fermented milk product as well as the *Lactococcus lactis* CNCM I-1631 bacterial strain with a deleted genomic SOD-A gene with expression complemented with a plasmid expressing SOD-A fermented milk product, ameliorated the colitis induced in the treated TRUC mice, as evidenced by histologic evaluation. In contrast, the administration of the *Lactococcus lactis* CNCM I-1631 bacterial strain with a deleted genomic SOD-A gene fermented milk product failed to ameliorate the induced colitis. The foregoing further evidences that the *L. lactis* CNCM I-1631 bacterial strains expressing SOD-A are capable of improving or otherwise ameliorating colitis in the TRUC mouse model in a SOD-A dependent fashion.

EXAMPLE 6

As previously discussed, the administration of dextran sodium sulfate results in epithelial damage and a robust inflammatory response in the colon lasting several days and is an established murine inflammatory injury model of acute colitis. The ability of the *Lactococcus lactis* CNCM I-1631 bacterial strain to affect histologic colitis scores in wild-type mice treated with dextran sodium sulfate for 5 days (experimental day 3 through 8) was also evaluated.

Wild-type mice were treated with dextran sodium sulfate and were administered a *Lactococcus lactis* CNCM I-1631 bacterial strain fermented milk product from experimental day 1-10 (n=5), a *Lactococcus lactis* CNCM I-1631 bacterial strain with a deleted genomic SOD-A gene fermented milk product from experimental day 1-10 (n=11), or a *Lactococcus lactis* CNCM I-1631 bacterial strain with a deleted genomic SOD-A gene with expression complemented with a plasmid expressing SOD-A fermented milk product from experimental day 1-10 (n=5).

After treatment the mice were sacrificed and their colons removed and dissected free from the anus to distal to the cecum, colonic contents removed, and colons cleaned with PBS prior to fixation in 4% PFA or 10% neutral buffered formalin followed by routine paraffin embedding. After paraffin embedding, 0.5 micrometer sections were cut, stained and examined. Colitis was assessed based on an assigned histological colitis score.

Figure 8:
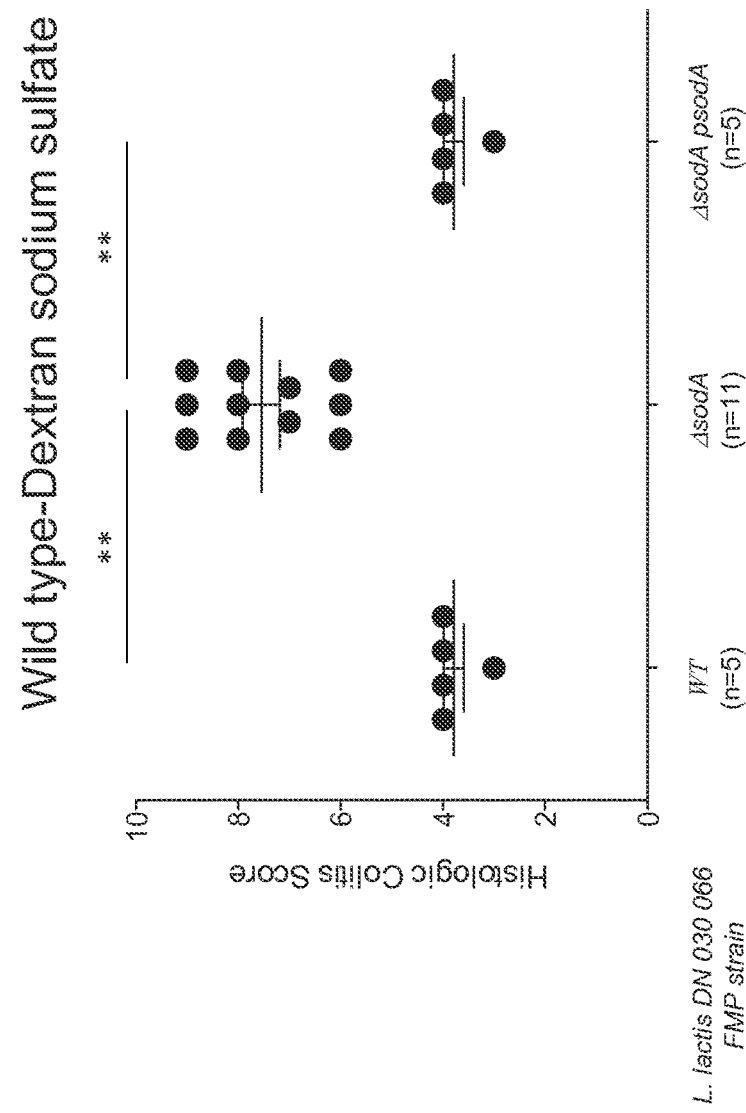
FIG. 8 illustrates histologic colitis scores for wild type mice treated with dextran sodium sulfate for 5 days (experimental day 3 through 8) and administered either a Lactococcus lactis CNCM I-1631 bacterial strain fermented milk product from experimental day 1-10, a Lactococcus lactis CNCM I-1631 bacterial strain with a deleted genomic SOD-A gene fermented milk product from experimental day 1-10, or a Lactococcus lactis CNCM I-1631 bacterial strain with a deleted genomic SOD-A gene with expression complemented with a plasmid expressing SOD-A fermented milk product from experimental day 1-10. A one-way ANOVA with Dunn's post-hoc test was performed to evaluate statistical significance, ** indicates the p-value<0.01.

As illustrated in FIG. 8, administration of both the wild-type *Lactococcus lactis* CNCM I-1631 bacterial strain fermented milk product and the *Lactococcus lactis* CNCM I-1631 bacterial strain with a deleted genomic SOD-A gene with expression complemented with a plasmid expressing SOD-A fermented milk product, ameliorated the colitis induced in the dextran sodium sulfate-treated mice as evidenced by histologic evaluation. In contrast, the administration of the *Lactococcus lactis* CNCM I-1631 bacterial strain with a deleted genomic SOD-A gene fermented milk product failed to ameliorate the dextran sodium sulfate-induced colitis. The foregoing provides further evidence that the *L. lactis* CNCM I-1631 bacterial strains expressing SOD-A are capable of improving or otherwise ameliorating colitis in the dextran sodium sulfate treated mice and that the observed effects occur in a SOD-A dependent fashion.

The foregoing studies therefore evidence that the administration *L. lactis*, and in particular the *L. lactis* CNCM I-1631 bacterial strain expressing SOD-A or of SOD-A isolated from *L. lactis* CNCM I-1631 can successfully reduce reactive oxygen species (ROS), reduce oxidative stress, and improve or otherwise ameliorate inflammatory bowel disease (e.g., colitis) and thereby treat, induce remission, and prevent relapse of inflammatory bowel disease.

What is claimed is:

1. A method of treating a subject having an inflammatory condition, wherein the method comprises administering an effective amount of a composition to the subject and thereby treating the inflammatory condition, wherein the composition comprises isolated bacteria of *Lactococcus lactis* strain CNCM I-1631.

2. The method of claim 1, wherein the inflammatory condition is induced by reactive oxygen species (ROS).

3. The method of claim 1, wherein the inflammatory condition is selected from the group consisting of inflammatory bowel disease, ulcerative colitis, Crohn's disease, diversion colitis, pouchitis, aging, cancers of the gastrointestinal tract, irritable bowel syndrome, obesity and type II diabetes mellitus.

4. A method of reducing reactive oxygen species (ROS)-induced damage to the gastrointestinal tract of a subject, wherein the method comprises administering to the subject a composition comprising isolated bacteria of *Lactococcus lactis* CNCM I-1631, thereby reducing the ROS-induced damage.

5. The method of claim 4, wherein the ROS-induced damage results from one or more conditions selected from the group consisting of inflammatory bowel disease, ulcerative colitis, diversion colitis, Crohn's disease, cancers of the gastrointestinal tract, irritable bowel syndrome, obesity and type II diabetes mellitus.

6. The method of claim 1 or 4, wherein the isolated *Lactococcus lactis* strain CNCM I-1631 expresses a superoxide dismutase-A (Sod-A) enzyme encoded by the nucleotide sequence of SEQ ID NO: 2.

7. The method of claim 1 or 4, wherein the isolated *Lactococcus lactis* strain CNCM I-1631 expresses a Sod-A enzyme encoded by the nucleotide sequence of SEQ ID NO: 3.

* * * * *